United States Patent
Nefzger et al.

(10) Patent No.: US 6,977,290 B2
(45) Date of Patent: Dec. 20, 2005

(54) PROCESS FOR PREPARING OLIGOMERIC ALIPHATIC DIOLS, POLYCARBONATEDIOLS BASED THEREON AND PREPOLYMERS THEREOF

(75) Inventors: Hartmut Nefzger, Pulheim (DE); Erika Bauer, Jüchen (DE); Manfred Schmidt, Dormagen (DE); Hans-Dieter Ruprecht, Köln (DE); James-Michael Barnes, Breitscheid (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/763,003

(22) Filed: Jan. 22, 2004

(65) Prior Publication Data

US 2004/0152861 A1   Aug. 5, 2004

(30) Foreign Application Priority Data

Jan. 31, 2003   (DE) ................................ 10 303 881

(51) Int. Cl.$^7$ ............................................. C08G 18/44
(52) U.S. Cl. .................... 528/85; 528/59; 528/370; 528/371; 528/425; 568/698; 568/699
(58) Field of Search ......................... 528/59, 85, 370, 528/371, 425; 568/698, 699

(56) References Cited

U.S. PATENT DOCUMENTS

| | | | |
|---|---|---|---|
| 3,022,272 A | * | 2/1962 | Schnell ........................ 528/198 |
| 3,631,200 A | | 12/1971 | Nehring et al. ............. 260/463 |
| 3,640,967 A | | 2/1972 | König et al. ................ 260/77.5 |
| 3,867,350 A | | 2/1975 | Pedain et al. ........ 260/77.5 AM |
| RE29,224 E | | 5/1977 | Pedain et al. ........ 260/77.5 AM |
| 4,105,641 A | | 8/1978 | Buysch et al. ............... 526/712 |
| 4,808,691 A | | 2/1989 | Konig et al. ................... 528/76 |
| 2004/0030095 A1 | * | 2/2004 | Sunkara et al. ............. 528/425 |

FOREIGN PATENT DOCUMENTS

| | | |
|---|---|---|
| CA | 1064957 | 10/1979 |
| DE | 857 948 | 12/1952 |
| GB | 1 263 225 | 2/1972 |
| GB | 1 270 077 | 4/1972 |

OTHER PUBLICATIONS

Research Disclosure; RD 484004; Catalyst Removal form Polyether Polols using Brine Extraction; Aug. 2004.*
Angew. Chem. 92 (month unavailable0 1980, pp. 742-743, Peter Ball et al, "Carbonate und Polycabonate aus Hamstoff und Alkohol".

* cited by examiner

*Primary Examiner*—Rachel Gorr
(74) *Attorney, Agent, or Firm*—Joseph C. Gil; John E. Mrozinski, Jr.

(57) ABSTRACT

The present invention relates to a method for preparing oligomeric aliphatic diols, polycarbonatediols based thereon and NCO-terminated prepolymers obtainable therefrom. The inventive compounds may find use in the preparation of polyurethanes.

12 Claims, No Drawings

PROCESS FOR PREPARING OLIGOMERIC ALIPHATIC DIOLS, POLYCARBONATEDIOLS BASED THEREON AND PREPOLYMERS THEREOF

FIELD OF THE INVENTION

The present invention provides a method for preparing oligomeric aliphatic diols, polycarbonatediols based thereon and NCO-terminated prepolymers obtainable therefrom, and also the use thereof to prepare polyurethanes.

BACKGROUND OF THE INVENTION

Aliphatic polycarbonate diols have been known for a long time. They can be prepared from non-vicinal diols by reaction with diaryl carbonates (DE-OS 19 15 908), dialkyl carbonates (DE-OS 25 55 805), dioxolanones (DE-OS 25 23 352), phosgene (DE-OS 15 95 446), bischloroformates (DE-OS 8 57 948) or urea (Angew. Chem. 92 (1980) 742). From among the many diols described for use in the literature, only 1,6-hexanediol or compounds derived from 1,6-hexanediol have been widely used on an industrial scale. Thus, for example, high-quality polyurethane elastomers and also lacquers are prepared using polycarbonatediols which are based on 1,6-hexanediol.

The resistance to hydrolysis of polyurethanes prepared from these types of polycarbonatediols is particularly outstanding. It exceeds that of analogous compounds made from polyadipatepolyols by far. Pure hexanediolpolycarbonates with number-average molecular weights of 500 to 5000 are waxy substances with a softening temperature range of approx. 45 to 55° C., depending on the molecular weight. Accordingly, the polyurethanes prepared from these have an elevated shear modulus at low temperatures, i.e. they lose their flexibility. For this reason, diols were developed which were intended to compensate for this disadvantage. The following may be mentioned, for example: oligoesters based on adipic acid (DE-AS 19 64 998), oligoesters based on caprolactone (DE-AS 17 70 245) or oligomeric tetraethylene glycols (DE-AS 22 21 751) and tetrabutylene glycols.

The disadvantage with these building blocks is their more readily hydrolyzable ester group and the elevated hydrophilicity, which at the least leads to a greater swelling of the PUR molded items prepared therefrom.

Another disadvantage of polycarbonatediols based on hexanediol is the comparatively high viscosity (approx; 5000 mPas at 60° C. with a number-average molecular weight of 2000 g/mol). This can lead to problems during processing to form polyurethane molded items.

According to the disclosure in U.S. Pat. No. 4,808,691, the disadvantages mentioned can be overcome by reacting oligomeric hexanediols with diphenyl carbonate in a stoichiometric ratio such that polycarbonatediols with number-average molecular weights of 500 to 12000, preferably 700 to 6000, result, wherein the degree of oligomerization of the ether is chosen in such a way that the ratio of ether to carbonate groups is 5:1 to 1:5, preferably 3:1 to 1:3.

However, on an industrial scale, the method for preparing oligomeric hexanediols disclosed in U.S. Pat. No. 4,808,691 proves time-consuming, labor-intensive and therefore costly. The method described in detail in that document requires the separation of water of reaction by distillation, wherein an entraining agent and catalysts are also used. Naphthaline-1,5-disulfonic acid is mentioned as the preferred catalyst. Toluene, xylene, gas oil fractions, cyclohexane, chlorobenzene and the oxepane also being formed as a secondary product are used as entraining agents, wherein the formation of this product can be slightly suppressed.

Working up after reaching the desired degree of oligomerization, detectable from the amount of water formed, is performed, according to U.S. Pat. No. 4,808,691, in such a way that the reaction mixture is cooled to 100° C. and the sulfonates present in the reaction mixture are hydrolyzed by adding 5–10% of water over 1–3 hours. The catalyst released is neutralized with aqueous alkali or ammonia, the water and other volatile components are distilled off and the catalyst, deposited as a salt, is filtered off.

On an industrial scale, however, this type of procedure has two serious disadvantages: the salt is produced in a form that can be isolated only in a very lengthy process. Typical filtration times for a batch of 3 tons are of the order of magnitude of 30 hours, wherein a change of filter is required every hour. Smaller batches of, for example, 200 kg require filtration times of approx. 5 hours.

The use of coarser filter materials which, although they facilitate faster filtration, lead to less effective separation of the salt, cannot be considered because even the smallest amount of this salt has a negative effect on the reaction of the polyols obtained to give polycarbonatediols.

Furthermore, it has been shown that oligomeric hexanediols prepared in accordance with U.S. Pat. No. 4,808,691 cannot then be used universally. Although they can react with diphenyl carbonate to give the corresponding polycarbonatediols under catalysis with bis(tributyltin) oxide or dibutyltin oxide, they do not react using heavy-metal-free catalysis, e.g. using basic salts of magnesium such as magnesium hydroxide carbonate. Even the slightest contamination with salts of sulfonic acid leads to incomplete building up of the polycarbonatediol.

The use of organotin-containing catalysts is therefore a particular disadvantage because they are not ecologically harmless.

Furthermore, oligomeric hexanediols prepared in accordance with U.S. Pat. No. 4,808,691 exhibit comparatively strong discoloration that is then carried through to the corresponding secondary-products, that is polyethercarbonatepolyols, their diisocyanate prepolymers and also the polyurethane molded items produced therefrom. This undesired discoloration represents yet another disadvantage.

Another disadvantage is that hydrolysis exclusively with water and ammonia can lead to incomplete hydrolysis of the sulfonates. If these esters decompose during the course of further reactions, then the sulfonic acid released can also cause incomplete reactions.

SUMMARY OF THE INVENTION

The present invention provides a process for preparing oligomeric diols, e.g. hexanediols, which both greatly simplifies preparation and also provides widely useable products, in particular those which can be reacted further using basic magnesium salts to give polycarbonatepolyols. In addition, the oligomeric diols obtained and their secondary products should exhibit greatly reduced discoloration.

These and other advantages and benefits of the present invention will be apparent from the Detailed Description of the Invention herein below.

DETAILED DESCRIPTION OF THE INVENTION

The present invention will now be described for purposes of illustration and not limitation. Except in the operating examples, or where otherwise indicated, all numbers expressing quantities, percentages, and so forth in the specification are to be understood as being modified in all instances by the term "about."

The inventors herein have found that separation of the catalyst is facilitated and products with improved quality are obtained by introducing a phase separation step to give an organic and an aqueous phase during working up of the reaction mixture.

The invention provides a process for preparing oligomeric aliphatic diols in which:
1. an aliphatic diol is oligomerized in the presence of an acid catalyst and an entraining agent and the water formed is distilled off azeotropically,
2. an aqueous base is added to the reaction mixture after reaching the desired degree of oligomerization and any esters formed during oligomerization are hydrolyzed,
3. the reaction mixture is adjusted to a pH of 4.0 to 8.0 by adding non oxidising inorganic acids or the salts thereof, and,
4. after phase separation of the reaction mixture, the organic phase is isolated, dewatered and filtered.

Aliphatic diols with a molecular weight of 100 to 200, preferably 118 to 175 g/mol are used as diols. 1,6-hexanediol, 3-methyl-1,3-pentanediol, 1,7-heptanediol, 1,8-octanediol, 1,9-nonanediol or 1,10-decanediol are preferably used, particularly preferably 1,6-hexanediol or mixtures of 1,6-hexanediol with up to 50 wt. % of other diols from the group including 3-methyl-1,3-pentanediol, 1,7-heptanediol, 1,8-octanediol, 1,9-nonanediol and 1,10-decanediol.

Catalysts used for diol oligomerization in the process according to the invention are strong acids with pKa values of <3, in amounts of 0.1 to 2 wt. %. Examples are inorganic acids such as sulfuric acid, phosphoric acid, hydrogen chloride, hydrogen bromide or hydrogen iodide and their aqueous solutions as well as organic acids such as butanesulfonic acid, benzenesulfonic acid, toluenesulfonic acid, benzenedisulfonic acid and naphthalinedisulfonic acid. Napthaline-1,5-disulfonic acid is preferably used.

Toluene, xylene, gas oil fractions, cyclohexane or chlorobenzene are used as entraining agents, toluene being preferred.

Oligomerization is preferably performed at temperatures of 150 to 200° C., a pressure of 700 to 1300 mbar, preferably atmospheric pressure, for a period of 5 to 25 hours, depending on the degree of oligomerization aimed at, the amount of catalyst used and the reaction temperature. The oligomerization reaction is preferably continued to a degree of oligomerization of 1.5 to 10.

In the process according to the invention, an aqueous inorganic base is added after completion of the oligomerization reaction and azeotropic separation of the water of reaction. The reaction mixture is preferably allowed to cool to about 100° C. before adding the base. Alkali metal hydroxides are preferably used as bases, particularly preferably potassium or sodium hydroxide. The bases used preferably have a water content of 5 to 50 wt. %. The amount of base added is preferably between the stoichiometric amount required for neutralization of the acid catalyst and twice that amount.

The hydrolysis, during oligomerization of the diol, of any esters formed due to reaction of the acid catalyst with hydroxyl groups in monomeric or oligomeric diols is preferably performed by stirring for at least one hour at elevated temperature, under atmospheric pressure or elevated pressure. If hydrolysis is performed at a temperature higher than 100° C., an elevated pressure is preferably applied. In practice, it has proven especially beneficial to hydrolyze for 2 to 5 hours at 90 to 100° C. under atmospheric pressure.

After completion of hydrolysis, the pH of the reaction mixture is adjusted to within the range 4.0 to 8.0, preferably 4.5 to 7.5, more preferably 5.5 to 7.0, by adding non-oxidizing inorganic acids or their salts. The reaction mixture is preferably first allowed to cool to room temperature. Acids, the salts of which are very soluble in water, are preferred. Sulfuric acid and its acid alkali metal salts and analogous phosphoric acid and carbonic acid compounds are preferred. The acids and their salts may be used in the pure form or as a solution in a solvent, in particular water.

The pH is preferably determined by adjusting 20 ml of a mixture of 9 parts of methanol and 1 part of water to a pH of 7.0, using 1/100 N NaOH or KOH, then stirring in 10 ml of the reaction mixture and reading off the pH after 5 minutes. A commercial pH meter with pH electrodes may be used for this purpose.

When a pH of 5.5 to 7.0 has been achieved, the stirrer is switched off and the mixture is left to separate into phases, an upper organic and a lower aqueous phase. In a preferred variant, salts which are readily soluble in water, preferably common salt, are added to accelerate phase separation, following final adjustment of the pH.

The aqueous phase is separated at 30–50° C. and then residual amounts of water and the entraining agent used in the condensation phase are removed from the remaining organic phase under reduced pressure (0.001–100 mbar) at elevated temperature (90–160° C.).

After cooling to 60–100° C., preferably 75–85° C., the organic phase is filtered on a pressure Nutsche filter, coated with a fine-pored filter paper (e.g. Suprasec-1000 from Seitz). A water-clear, slightly yellow liquid is obtained. The filtration time for a 3-tonne batch is approx. 3–4 hours.

Oligomeric diols obtained according to the invention are particularly suitable for preparing polycarbonatediols. Therefore, the invention also provides a process for preparing polycarbonatediols in which an oligomeric diol obtained by the process according to the invention, optionally after adding monomeric diol, in particular 1,6-hexanediol, to adjust the degree of oligomerization, is reacted with a sub-stoichiometric amount of a carbonate donor such as diphenyl carbonate, dimethyl carbonate or phosgene in the presence of a catalyst. Diphenyl carbonate is preferably used as the carbonate donor.

The molecular weight of the polycarbonatediol can be varied between wide limits by varying the stoichiometric ratios used of oligomeric diol, monomeric diol and carbonate donor. However, polycarbonatediols with number-average molecular weights of 800 to 2800, particularly preferably 1500 to 2500 g/mol, are preferable.

Heavy metal-free catalysts are preferably used as catalysts. Magnesium salts are particularly preferable, in particular magnesium hydroxide carbonate. Further details of the method of preparation of polycarbonatepolyols according to the invention are disclosed in DE-OS 101 25 557.

If the reaction is performed in the presence of a basic magnesium salt as catalyst, this is subsequently neutralized by adding acids. Examples of acids that can be used are tartaric acid, citric acid, dibutyl phosphate, phosphoric acid, sulfuric acid and their acid salts. Sulfuric acid is preferably used to neutralize the basic magnesium catalyst, wherein a clear solution is obtained. Separation from the product of the magnesium sulfate formed is not required because this behaves in an inert manner during further reaction of the polycarbonatediol.

The invention also provides a process for preparing NCO-terminated prepolymers from polycarbonatediols obtained in accordance with the invention. Here, a polycarbonatediol obtained by the process according to the invention is reacted in sub-stoichiometric amounts with a polyisocyanate. The polyisocyanates used are preferably diisocyanates from the group including diphenylmethane diisocyanate, napthaline-1,4-diisocyanate, naphthaline-1,5-diisocyanate, durene diisocyanate, toluene diisocyanate, hexamethylene-1,6-diisocyanate and isophorone diisocyanate. 4,4'-diphenylmethane diisocyanate (e.g. DESMODUR 44M, Bayer AG) and mixtures of this with 2,4'- and 2,2'-diphenylmethane diisocyanate, wherein the proportion of the latter compounds amounts to less than 10 wt. %, are particularly preferred. Prepolymers according to the invention are characterized by substantially improved storage stability as compared with those of the art.

EXAMPLES

Preparation of Oligomeric Hexanediols

Example 1

240 kg (2069 moles) of molten hexanediol were mixed with 2.5 kg of aqueous 1,5-naphthalinedisulfonic acid (35 wt. % strength) and 10 kg of toluene, with stirring, in a 300-liter VA tank with a column and azeotropic cap, reflux condenser and distillation receiver. The temperature was raised to 170° C. and 22 kg of water distilled off over the course of 10 hours under a slight stream of nitrogen.

The tank was cooled to 100° C., evacuated and 10 kg of distilled water was drawn in under the residual vacuum. After the contents of the tank were cooled to 30° C., 0.908 kg of aqueous caustic soda solution (32 wt. % strength) were added and the mixture was heated to 100° C. over the course of 2 hours. The mixture was stirred for 1 hour at 100° C., cooled to 50° C. and 103 g of concentrated aqueous sodium hydrogen sulfate solution were then added and stirring continued for another 30 min. at this temperature. The pH of the reaction mixture was 6.4, the acid value was 0.05 mg KOH/g.

Then the mixture was cooled to 30° C. and 44 kg of aqueous common salt solution (10 wt. % strength) were stirred in intensively. After switching off the stirrer, the phases separated within approx 30 min.; the lower phase was run off. The product remaining in the tank was dewatered by applying a vacuum (1 mbar) at 140° C. for 3 hours and then cooled to 80° C. The mixture was filtered within 40 minutes on a Seitz filter with a Supra 5500 filter plate.

The yield was 190 kg, the water content of the product was 0.02 wt. %, the hydroxyl value was 466 mg KOH/g and the acid value was 0.05 mg KOH/g.

Example 2 (Comparison)

240 kg (2069 moles) of molten hexanediol were mixed with 2.5 kg of aqueous 1,5-naphthalinedisulfonic acid (35 wt. % strength) and 10 kg of toluene, with stirring, in a 300-liter VA tank with a column and azeotropic cap, reflux condenser and distillation receiver. The temperature was raised to 170° C. and 21.105 kg of water distilled off over the course of 10 hours under a slight stream of nitrogen. The experimentally determined hydroxyl value at this point in time was 431 mg KOH/g.

The tank was cooled to 100° C., evacuated and 10 kg of distilled water was drawn in under the residual vacuum. After cooling the contents of the tank to 30° C., 0.9 kg of ammonia water were added and the mixture was heated to 80° C. over the course of 3 hours. After this temperature was reached, a vacuum was slowly applied, wherein the distillation of water was triggered at 350 mbar. When 15 mbar, had been reached, the temperature was increased stepwise to 140° C. and the pressure was lowered to 2 mbar using an oil pump. Stirring was continued for a further hour under these conditions, then the temperature was reduced to 80° C. and the tank was aerated. The mixture was filtered within 320 minutes on a Seitz filter with a Supra 5500 filter plate, wherein a change of filter was required after approx. every 45 minutes.

The yield was 201 kg, the water content of the product was 0.02 wt. %, the hydroxyl value was 486 mg KOH/g and the acid value was 0.05 mg KOH/g.

Preparation of Polycarbonatediols

Example 3

3000 g of the oligomeric hexanediol prepared in example 1 were reacted with 1107 g of hexanediol and 4157 g of diphenyl carbonate in the presence of 150 mg of magnesium carbonate hydroxide pentahydrate. The reaction mixture was heated for one hour at 180° C., cooled to 120° C. and then the temperature was raised to 200° C. over the course of 6 hours, wherein the pressure was 15 mbar from approx. 120° C. To complete the reaction, stirring was continued for 2 hours at 200° C. and a pressure of <1 mbar. A total of 3652 g of phenol were distilled off. For neutralization of the basic magnesium catalyst, 175 mg of concentrated sulfuric acid were added. 4600 g of polycarbonatediol were obtained.

The OH value of the polycarbonatediol was 57.9 mg KOH/g, the acid value was 0.12 mg KOH/g, the viscosity (according to DIN 53015) was 1100 mPas (75° C.). UV-spectroscopic determination of the terminal groups showed a concentration of <0.01 wt. % of phenylcarbonato groups, 0.14 wt. % of phenoxy groups and 0.02 wt. % of free phenol.

Example 4 (Comparison)

1800 g of oligomeric hexanediol with an OH value of 501 mg KOH/g, prepared according to the process described in U.S. Pat. No. 4,808,691, were reacted with 448 g of hexanediol and 2274 g of diphenyl carbonate in the presence of 70 mg of dibutyltin oxide. The reaction mixture was heated for one hour at 180° C., cooled to 120° C. and then the temperature was raised to 200° C. over the course of 6 hours, wherein the pressure was 15 mbar from approx. 120° C. To complete the reaction, stirring was continued for 2 hours at 200° C. and a pressure of <1 mbar. A total of 2002 g (contaminated with hexanediol) of phenol were distilled off and 2520 g of polycarbonatepolyol with an OH value of 48.0 g KOH/g were obtained.

The OH value of the polyethercarbonatepolyol was increased to 56.6 mg KOH/g by adding 22.5 g of hexanediol and incorporating this into the polymer by esterification. The acid value of the product was 0.2 mg KOH/g, the viscosity (according to DIN 53015) was 900 mPas (75° C.), the color index was >999 Haze. The hexanediol post-batch thus produced the target OH value, but the elimination of phenol was incomplete. The result of this is the clear and undesirable downwards shift in the viscosity.

Example 5 (Comparison)

1556 g of oligomeric hexanediol with an OH value of 501 mg KOH/g, prepared according to the process described in U.S. Pat. No. 4,808,691, were reacted with 426 g of hexanediol and 2005 g of diphenyl carbonate in the presence of 358 mg of magnesium carbonate hydroxide pentahydrate. The reaction mixture was heated for one hour to 180° C., cooled to 120° C. and then the temperature was raised to 200° C. over the course of 6 hours, wherein the pressure was 15 mbar from approx. 120° C.

No phenol could be distilled off.

Preparation of NCO-Terminated Prepolymers

Example 6 (Comparison)

781.8 kg of pure diphenylmethane diisocyanate (DESMODUR 44 M, Bayer AG) were reacted with 1300 kg of a polycarbonatediol prepared in accordance with (comparison) example 4 for two hours at 80° C. An NCO-terminated prepolymer with an NCO content (according to DIN 53185) of 9.95 wt. % and a viscosity of 1920 mPas (70° C.) (according to DIN 53015) was obtained.

To determine the storage-stability, a sample of the prepolymer was stored for three days under $N_2$ at 80° C. in the drying cabinet. After this storage procedure, the viscosity had risen by approx. 26% to 2420 mPas (70° C.) and the NCO content had dropped to 9.73 wt. %.

Example 7

41.4 kg of pure diphenylmethane diisocyanate (DESMODUR 44 M, Bayer AG) were reacted with 68.6 kg of a polycarbonatediol prepared in accordance with example 3 for two hours at 80° C. An NCO-terminated prepolymer with an NCO content (according to DIN 53185) of 9.91 wt. % and a viscosity of 1910 mPas (70° C.) (according to DIN 53015) was obtained.

To determine the storage-stability, a sample of the prepolymer was stored for three days under $N_2$ at 80° C. in the drying cabinet. After this storage procedure, the viscosity had risen by approx. 9.5% to 2090 mPas (70° C.) and the NCO content had dropped to 9.77 wt. %.

Storage for three days at 80° C. simulates storage at room temperature for a longer period (approx. 6 months, see G. M. Barrow: "Physikalische Chemie", part III, Vieweg Verlag, Braunschweig 1970, p. 296). The measurements performed show that prepolymers prepared from polycarbonatediols according to the invention are 3-times more storage-stable than conventionally prepared prepolymers.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing oligomeric aliphatic diols comprising:
    oligomerizing an aliphatic diol in the presence of an acid catalyst and an entraining agent, wherein the water formed is distilled off azeotropically,
    adding an aqueous base to the reaction mixture after reaching the desired degree of oligomerization and hydrolyzing any esters formed during oligomerization,
    adjusting the pH of the reaction mixture of 4.0 to 8.0 by adding non-oxidizing inorganic acids or the salts thereof, and,
    isolating, dewatering and filtering the organic phase after phase separation of the reaction mixture.

2. A process for preparing polycarbonatediols comprising reacting an oligomeric aliphatic diol prepared according to claim 1 with a sub-stoichiometric amount of a carbonate donor in the presence of a catalyst.

3. The process according to claim 2 wherein the catalyst comprises a basic magnesium salt.

4. The process according to claim 2 wherein the carbonate donor comprises diphenyl carbonate.

5. A process for preparing NCO-terminated prepolymers comprising reacting sub-stoichiometric amounts of the polycarbonatediol made according to claim 3 with a polyisocyanate.

6. The process according to claim 5 wherein the polyisocyanate comprises diphenylmethane diisocyanate.

7. In a process of preparing polyurethane, the improvement comprising incorporating at least one oligomeric aliphatic diol made according to claim 1.

8. In a process of preparing polyurethane, the improvement comprising incorporating at least one NCO-terminated prepolymer made according to claim 5.

9. The process according to claim 1 wherein the diol is chosen from 1,6-hexanediol, 3-methyl-1,3-pentanediol, 1,7-heptanediol, 1,8-octanediol, 1,9-nonanediol and 1,10-decanediol.

10. The process according to claim 1 wherein the acid catalyst is chosen from sulfuric acid, phosphoric acid, hydrogen chloride, hydrogen bromide, hydrogen iodide and aqueous solutions thereof, butanesulfonic acid, benzenesulfonic acid, toluenesulfonic acid, benzenedisulfonic acid and naphthalinedisulfonic acid.

11. The process according to claim 1 wherein the entraining agent is chosen from toluene, xylene, gas oil fractions, cyclohexane and chlorobenzene.

12. The process according to claim 1 wherein the aqueous base is chosen from alkali metal hydroxides.

* * * * *